United States Patent
Dunworth et al.

(10) Patent No.: US 9,622,880 B2
(45) Date of Patent: Apr. 18, 2017

(54) MESENCHYMAL CELL-BASED SOFT FUSION AS A BIOLOGICAL INTERVERTEBRAL DISC REPLACEMENT

(71) Applicant: SpineSmith Partners, L.P., Austin, TX (US)

(72) Inventors: Kevin Dunworth, Austin, TX (US); Matthew Murphy, Austin, TX (US); Theodore Sand, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 36 days.

(21) Appl. No.: 14/061,617

(22) Filed: Oct. 23, 2013

(65) Prior Publication Data

US 2014/0114419 A1    Apr. 24, 2014

Related U.S. Application Data

(60) Provisional application No. 61/717,440, filed on Oct. 23, 2012.

(51) Int. Cl.
*A61F 2/44*    (2006.01)
*A61F 2/28*    (2006.01)
*A61F 2/30*    (2006.01)

(52) U.S. Cl.
CPC .......... *A61F 2/4465* (2013.01); *A61F 2/442* (2013.01); *A61F 2002/2817* (2013.01); *A61F 2002/2835* (2013.01); *A61F 2002/2842* (2013.01); *A61F 2002/2867* (2013.01); *A61F 2002/30014* (2013.01); *A61F 2002/30069* (2013.01); *A61F 2002/30204* (2013.01); *A61F 2002/4475* (2013.01); *A61F 2310/00293* (2013.01)

(58) Field of Classification Search
CPC ...................... A61F 2/4455; A61F 2002/2835
USPC .................... 606/246–249; 623/17.11–17.16
See application file for complete search history.

(56) References Cited

U.S. PATENT DOCUMENTS

2010/0278891 A1*  11/2010  Ringeisen ............. A61B 17/80
                                                        424/422

* cited by examiner

*Primary Examiner* — Ellen C Hammond
(74) *Attorney, Agent, or Firm* — Winstead PC

(57) ABSTRACT

The invention comprises a combination of biological elements that will naturally remodel in vivo based on applied mechanical forces. The final composition will possess mechanical properties similar to cartilage or a disc, and significantly less stiff than bone or implants comprised of metals or plastics. The equilibrium stress conduction will minimize unnatural forces on neighboring healthy discs.

19 Claims, 2 Drawing Sheets

MESENCHYMAL CELL-BASED SOFT FUSION AS A BIOLOGICAL INTERVERTEBRAL DISC REPLACEMENT

CROSS-REFERENCES TO RELATED APPLICATIONS

This Application claims the benefit under 35 U.S.C. §119(e) of U.S. Provisional Patent Application No. 61/717,440 filed Oct. 23, 2012 which is incorporated herein by reference in its entirety as if fully set forth herein.

BACKGROUND OF THE INVENTION

Degenerated, herniated, or otherwise diseased intervertebral discs cause excruciating pain and are usually treated by discectomy (surgical removal of the disc). The newly formed defect is mechanically stabilized by hardware (plates, screws, intervertebral cages, etc.). Many surgeons attempt to biologically stabilize the defect by forming bone between the vertebral bodies, called a spinal fusion. Successful fusions result in a loss of flexibility at the intervertebral joint and put unnatural stresses on neighboring discs, eventually leading to their degeneration. The described invention will create a tissue with cartilage-like biomechanical properties less than that of bone, permitting a more natural transmission and distribution of weight loads throughout the spine.

SUMMARY OF THE INVENTION

The invention comprises a combination of biological elements that will naturally remodel in vivo based on applied mechanical forces. The final composition will possess mechanical properties similar to cartilage or a disc, and significantly less stiff than bone or implants comprised of metals or plastics. The equilibrium stress conduction will minimize unnatural forces on neighboring healthy discs. Because the implant is a living tissue, it will remodel and adapt over time. In a particular embodiment of the invention, the limitation to autologous cells and disc material will minimize the risk of disease transmission or infection.

DETAILED DESCRIPTION OF EXEMPLARY EMBODIMENTS

Figure 1A:
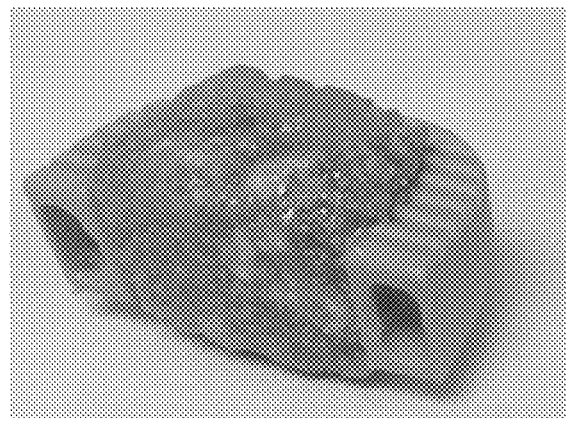
FIGS. 1A and 1B show soft fusion masses prepared with intervertebral disc fragments in accordance with an embodiment of the invention; and, FIG. 2 shows soft fusion material that is packed in the interbody space between lumbar vertebrae after disectomy in accordance with an embodiment of the invention.

An embodiment of the invention is directed to a method of creating a soft fusion between vertebral bodies. Following the removal of a damaged or painful intervertebral disc (discectomy), the surgeon minces or macerates the disc into fragments smaller than 5 mm. Disc fragments are combined with mesenchymal or progenitor cells and a rigid scaffold. These materials may also be combined with a binding agent. The cells may be autologous or allogenic and may be derived from bone, bone marrow, adipose or intervertebral disc tissue. The function of the cells is to modulate inflammation, deposit new extracellular matrix proteins, recruit endogenous cells and blood vessels by secretion and diffusion of growth factors, and remodel the consolidated tissue over time. The function of the disc fragments is to provide pro-cartilage cues to the cells present within the consolidated mass. The function of the rigid scaffold is to provide mechanical stiffness to the consolidated mass and a binding site for cells. The scaffold may be monolithic or as granules. The scaffold may be porous. The scaffold may have osteoconductive or chondroconductive properties.

In an embodiment, the scaffold is composed of calcium phosphate, more specifically hydroxyapatite. The binding agent bonds the various elements together and improves the implant's handling properties. An excellent example of a binding agent is fibrin, which can be derived from blood plasma, recombinant fibrinogen, or an animal source. In an embodiment, plasma protein concentrate derived from autologous platelet-poor plasma is combined with thrombin and calcium chloride and used as a binding agent.

Over a period of months to years, the soft fusion tissue adjusts to the appropriate structure and density based on the forces experienced at the specific spinal level. The surgeon may concurrently stabilize the vertebral bodies adjacent to the replaced disc using an interbody cage, a plate, and/or screws. The fixation mechanism should have compressive and tensile properties less than a vertebral body to provide a more natural shock absorption and flexibility at the joint. The principle of the invention is to allow the cells and tissue to remodel to conform with natural forces exhibited as described by Wolff's Law and Davis' Law. Wolff's Law describes the reorganization of cortical and trabecular bone tissue to become harder under repeated high stress (e.g. weight lifters) and less dense under low stress (e.g. astronauts in space). Davis' Law describes the reorganization of soft tissue and collagen matrices based on mechanical loads, analogous to Wolff's Law. The compressive strength and Young's (tensile) modulus for common spine implant materials and tissues are listed in Table 1.

Table 1 sets forth the approximate compressive strength and tensile modulus for spinal implant materials and native tissues. Soft Fusion masses should have mechanical properties that are in the range between the native vertebral body and intervertebral disc annulus.

TABLE 1

| Material | Compression Strength (MPa) | Tensile Modulus (MPa) |
| --- | --- | --- |
| Stainless Steel | 200,000 | 200,000 |
| Titanium | 125,000 | 120.000 |
| Bone Cement (PMMA) | 3,000 | 10,000 |
| Cortical Bone | 150-250 | 15,000 |
| PEEK | 10-30 | 4,000 |
| Total Vertebral Body | 10 | 12,000 |
| Cancellous Bone | 5 | 3,000 |
| Disc. Annulus | 0.1 | 6.5-20 |

In an embodiment of the invention, the soft fusion mass has a compressive strength and tensile modulus between the values of a total vertebral body and a disc annulus. Mechanical properties stiffer than a typical vertebral body will create a focal point for stresses in the consolidated tissue, prevent flexion between the adjacent vertebral bodies, and shield stresses imparted on the vertebral bodies which can lead to bone resorption. The soft fusion mass may be implanted interbody or posterolaterally.

Examples of demonstrated use of the claimed invention:
1. A soft fusion mass in accordance with an embodiment of the invention was prepared using disc fragments, polymer granules, porous hydroxyapatite granules, and platelet-poor plasma (PPP) (FIG. 1A). The mass was loaded within a lumbar interbody cage comprised of (PEEK) polymer.

Figure 1B:
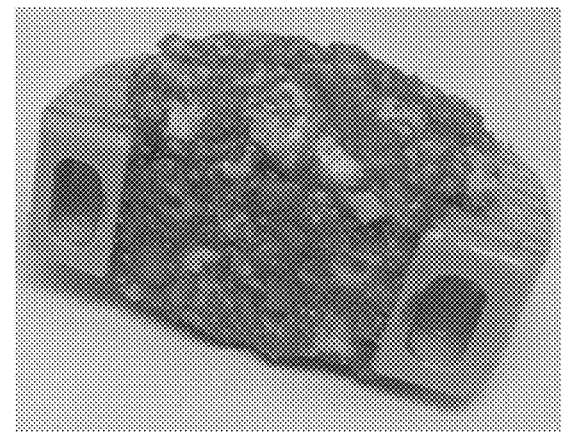

2. A soft fusion mass was prepared using disc fragments, porous hydroxyapatite granules, and plasma protein concentrate (PPC) clotted with thrombin and calcium chloride (FIG. 1B). The mass was loaded within a lumbar interbody cage comprised of PEEK polymer.

Figure 2:
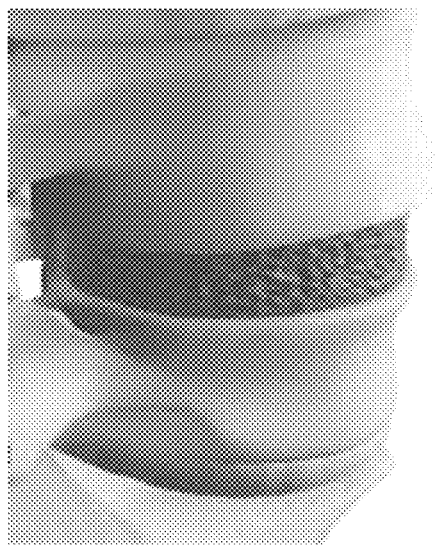

3. Soft Fusion elements of disc fragments, calcium phosphate powder, and bone marrow concentrate are packed directly into the interbody space (FIG. 2). The adjacent vertebral bodies are stabilized by posterior screws that permit micro-motion.

4. A Soft Fusion mass may be implanted in the posterolateral gutters for a posterior fusion. In this example, a combination of autologous bone marrow concentrate, disc material, allograft cancellous bone chips, and PPP clotted with thrombin was implanted. 18 months after implantation, histology of the fusion biopsy demonstrates a consolidated tissue with properties of both bone and cartilage (not shown).

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

What is claimed is:

1. A method of creating a fusion between vertebral bodies, the method comprising the steps of:
   removing a portion of an intervertebral disc;
   macerating, after the removing, the portion of the intervertebral disc to create disc fragments;
   combining the disc fragments with mesenchymal or progenitor cells, a scaffold, and optionally a binding agent to form a fusion composition;
   loading the fusion composition within an area or a junction between vertebral bodies; and
   subjecting the fusion composition to a level of pressure and force to promote fusion between the vertebral bodies of a patient.

2. The method of claim 1, wherein the scaffold is a rigid scaffold.

3. The method of claim 1, wherein the scaffold is a porous scaffold.

4. The method of claim 1, wherein the scaffold comprises hydroxyapatite.

5. The method of claim 1, wherein the scaffold is comprised of calcium phosphate.

6. The method of claim 1, wherein the binding agent comprises fibrin.

7. The method of claim 1, wherein the fusion composition has a compressive strength of less than 10 MPa.

8. The method of claim 1, wherein the fusion composition has a tensile strength of less than 12,000 MPa.

9. The method of claim 1, further comprising:
   wherein the disc fragments, the mesenchymal or progenitor cells, and optionally the binding agent form a soft fusion mass; and
   wherein the soft fusion mass has a compressive strength between 0.1 MPa and 10 MPa.

10. The method of claim 1, further comprising:
    wherein the disc fragments, the mesenchymal or progenitor cells, and optionally the binding agent form a soft fusion mass; and
    wherein the soft fusion mass has a tensile strength between 6.5 MPa and 12,000 MPa.

11. The method of claim 1, further comprising:
    wherein the disc fragments, the mesenchymal or progenitor cells, and optionally the binding agent form a soft fusion mass; and
    wherein the soft fusion mass further comprises autologous bone marrow concentrate, allograft cancellous bone chips, and platelet poor plasma that has been clotted with thrombin.

12. A fusion composition comprising:
    mascerated fragments of a spinal disc;
    mesenchymal or progenitor cells;
    a scaffold;
    wherein said composition is used to promote fusion between vertebral bodies and form a load bearing mass; and
    wherein the fusion composition has a compressive strength of less than 10 MPa.

13. The fusion composition of claim 12, wherein the scaffold is comprised of calcium phosphate.

14. The fusion composition of claim 12, further comprising a binding agent.

15. The fusion composition of claim 14, wherein the binding agent comprises fibrin.

16. The fusion composition of claim 12, wherein the fusion composition has a tensile strength of less than 12,000 MPa.

17. The fusion composition of claim 12, further comprising wherein the disc fragments, the mesenchymal or progenitor cells, and optionally a binding agent form a soft fusion mass.

18. The fusion composition of claim 12, further comprising:
    wherein the disc fragments, the mesenchymal or progenitor cells, and optionally a binding agent form a soft fusion mass; and
    wherein the soft fusion mass has a tensile strength between 6.5 MPa and 12,000 MPa.

19. The fusion composition of claim 12, further comprising:
    wherein the disc fragments, the mesenchymal or progenitor cells, and optionally a binding agent form a soft fusion mass; and
    wherein the soft fusion mass further comprises autologous bone marrow concentrate, allograft cancellous bone chips, and platelet poor plasma that has been clotted with thrombin.

\* \* \* \* \*